United States Patent [19]

van Andel

[11] Patent Number: Plant 6,474

[45] Date of Patent: Dec. 20, 1988

[54] ALSTROEMERIA VARIETY 'STARONIC'

[75] Inventor: Jacob van Andel, Aalsmeer, Netherlands

[73] Assignee: Van Staaveren, B.V., Aalsmeer, Netherlands

[21] Appl. No.: 23,762

[22] Filed: Mar. 9, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of Alstroemeria characterized by the generally light purple coloration of the outer petals of its very large blooms, each of which has a streak of darker purplish color extending from end-to-end along each side of its central groove and being occasionally marked with streaks of purplish color extending from the inner body portion to the petal margin; the inner petals being more narrow in form and being mainly of a yellow coloration, except for the petal tips, and being marked overall with short, deep purplish pencil stripes which spread longitudinally from the petal base to its tip. This plant is further distinguished by its vigorous, upright and strong growth habit, a very good winter production, and a more rapid growth habit, reaching a height of about 200 cm.

1 Drawing Sheet

BACKGROUND OF THE NEW PLANT

This new Alstroemeria plant originated as a seedling of a hybrid resulting from my crossing the variety 'Edison' (unpatented) as the seed parent and, as the pollen parent, a plant selected from my stock of plants maintained for breeding purposes at Aalsmeer, The Netherlands. This particular seedling was selected by me for propagation and test because of its very fast growth habit and its very large flowers of a distinctively different coloration than that of its companion variety 'Stalbel', which is from the same seed parent. Asexual propagation by root division was done under my direction at Aalsmeer and the resulting plant appearing to have the desirable characteristics of the parent, propagation of the new plant by root division was carried on through several successive generations, which demonstrated that the novel and distinctive characteristics of this new variety would hold true from generation to generation and appeared to be firmly fixed for continuous asexual propagation.

DESCRIPTION OF THE DRAWING

This new Alstroemeria hybrid is illustrated by the accompanying photographic drawing which, in full color, shows flowers of a blooming umbel of the plant and demonstrates the unique and distinctive color and form of the flowers, the color rendition being as nearly true to those specified as is possible to obtain by conventional photographic procedures.

DESCRIPTION OF THE NEW PLANT

The following is a detailed description of my new Alstroemeria hybrid as observed at Aalsmeer, The Netherlands, the color designations being according to The R.H.S. Colour Chart published in 1966 by The Royal Horticultural Society of London, England.

THE PLANT

Origin: Seedling.

Parentage:

*Seed parent.*—The variety 'Edison' (unpatented).

*Pollen parent.*—Breeding Stock Plant No. 1173-11 (unnamed and unpatented) selected from my collection of distinctive plants maintained for breeding purposes at Aalsmeer, The Netherlands.

Classification: Alstroemeria hybrid.

Form: Tall and erect bush.

Height: Up to about 200 cm.

Main stem:

*Length.*—From about 150 to 200 cm., depending upon season.

*Growth: Strong, vigorous and upright.*

Foliage:

*Quantity.*—Medium.

*Number of leaves.*—About 35 to 40, or more, depending on season.

*Size of leaf.*—Depending on season.

*Shape.*—Elliptic, with entire margins.

*Texture.*—Leathery.

*Color.*—Upper side — Middle Green. Under side — Middle Gray/Green.

Rhizomes:

*Size.*—Varying with age of plant.

*Color.*—White.

THE BUD

Size: Large.

*Diameter.*—About 1.5 cm.

*Length.*—About 4 cm.

Shape: Pear shaped.

Calyx: This plant has no calyx, the six petals of the flower being perianth and dividing simultaneously.

Peduncle:
*Length.*—About 15 cm.
*Character.*—Erect.
*Color.*—Green.

THE FLOWER

Blooming habit: Continuous throughout the year.
Flower size: Very large.
*Diameter.*—About 6 cm.
*Depth.*—About 5 cm.
Borne: Singly, in an umbel formation.
Shape: Funnel-like with petals curling outwardly.
Petalage:
*Number of petals.*—Six.
*Arrangement.*—Two concentric groups, each of three petals.
*Form.*—The outer petals are obovate with emarginate tips and entire margins. Inner petals are generally long, ovate with acute tips and entire margins.
Texture: Leathery.
Appearance: Shiny.
Color:
*Outer petals.*—Upper side — 56B. Reverse side — 56B.
*Inner petals.*—Top side — Generally 12B with 56B at the base and outer end. Reverse side — Generally the same as the top side.
Peduncle:
*Length.*—About 1 cm.
*Color.*—Middle green.

Persistence: The flowers hang on and dry.
Lasting quality:
*On the plant.*—About 21 days.
*As a cut flower.*—About 15 days.

REPRODUCTIVE ORGANS

Stamens:
*Number.*—Six.
*Arrangement.*—Normal.
*Anthers.*—Color: Gray/green.
*Pollen.*—Color: Dark blue/gray.
*Filaments.*—Length: About 4.5 cm. Color: Light pink.
Pistil:
*Number.*—One.
*Style.*—Length: Varies with age. Color: Pink/-white.
Stigma:
*Color.*—Pink.

This new plant most nearly resembles its companion 'Stalbel' (U.S. plant patent pending) but is distinguished by its novel flower color and more rapid growth habit.

I claim:

1. The new and distinctive Alstroemeria and the parts thereof, substantially as herein shown and described, particularly distinguished by the large size and light purple coloring of its flowers, by its vigorous and rapid growth habit, and by its good winter production.

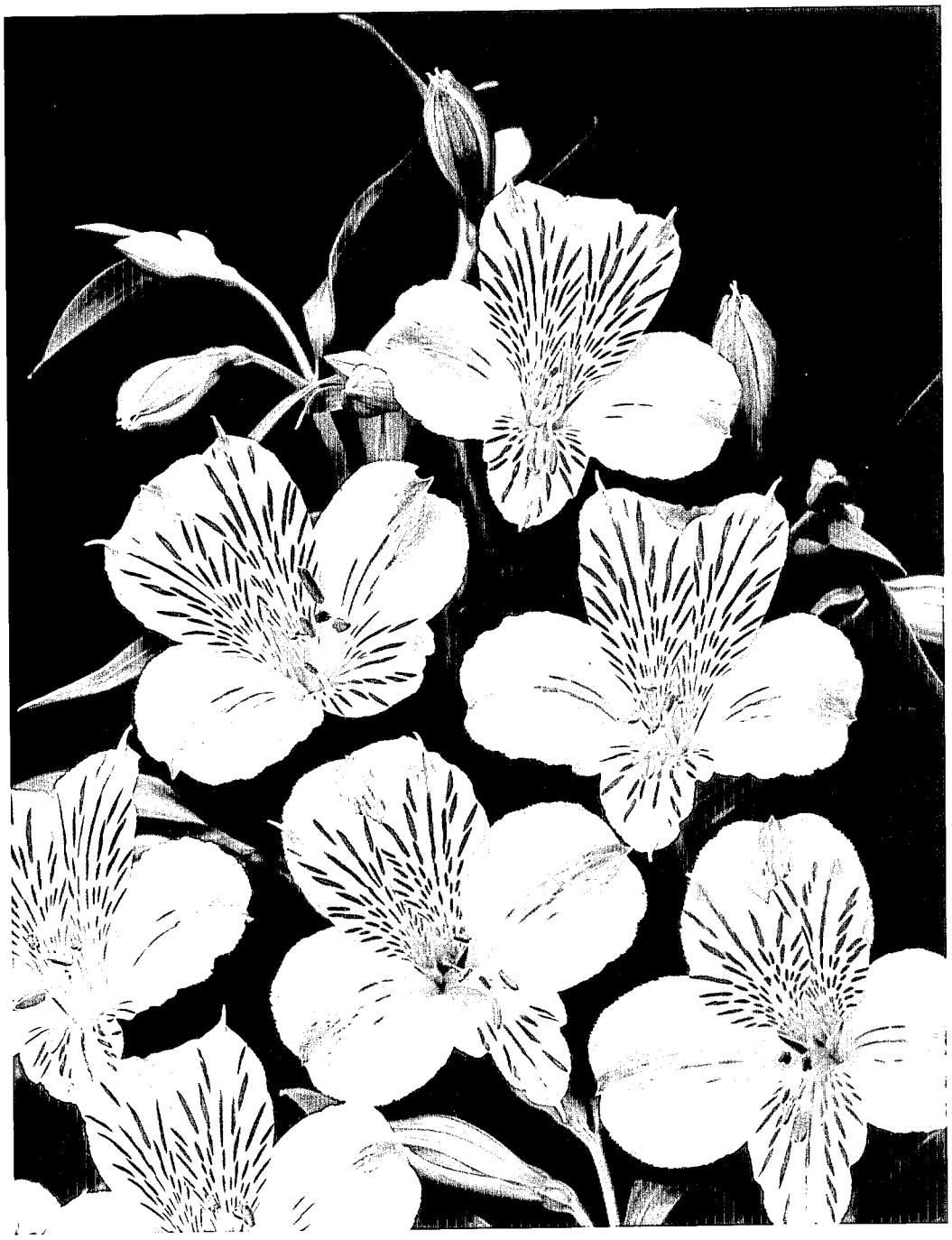

* * * * *